United States Patent
Mawn et al.

(10) Patent No.: US 8,403,828 B2
(45) Date of Patent: Mar. 26, 2013

(54) OPHTHALMIC ORBITAL SURGERY APPARATUS AND METHOD AND IMAGE-GUIDE NAVIGATION SYSTEM

(75) Inventors: Louise A. Mawn, Nashville, TN (US); Robert L. Galloway, Jr., Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1994 days.

(21) Appl. No.: 10/895,635

(22) Filed: Jul. 21, 2004

(65) Prior Publication Data

US 2005/0054900 A1 Mar. 10, 2005

Related U.S. Application Data

(60) Provisional application No. 60/488,758, filed on Jul. 21, 2003.

(51) Int. Cl.
 *A61B 1/00* (2006.01)
 *A61B 1/04* (2006.01)
(52) U.S. Cl. ........................................ 600/117; 600/103
(58) Field of Classification Search .................. 600/103, 600/109, 117–118, 145
 See application file for complete search history.

(56) References Cited

U.S. PATENT DOCUMENTS

| | | | | |
|---|---|---|---|---|
| 5,123,902 A * | 6/1992 | Muller et al. | .................... | 604/21 |
| 5,142,930 A | 9/1992 | Allen et al. | | |
| 5,403,306 A * | 4/1995 | Edwards et al. | ................... | 606/3 |
| 5,815,627 A * | 9/1998 | Harrington | .................... | 385/125 |
| 5,879,288 A * | 3/1999 | Suzuki et al. | ................. | 600/176 |
| 6,167,296 A * | 12/2000 | Shahidi | ......................... | 600/427 |
| 6,346,940 B1 * | 2/2002 | Fukunaga | ..................... | 345/427 |
| 6,500,114 B1 * | 12/2002 | Petitto et al. | ................... | 600/156 |
| 6,591,130 B2 * | 7/2003 | Shahidi | ......................... | 600/424 |
| 6,607,527 B1 * | 8/2003 | Ruiz et al. | ....................... | 606/41 |
| 7,809,421 B1 * | 10/2010 | Govari | ........................... | 600/407 |
| 2002/0007108 A1 * | 1/2002 | Chen et al. | ..................... | 600/117 |
| 2002/0010384 A1 * | 1/2002 | Shahidi et al. | ................ | 600/118 |
| 2002/0188194 A1 * | 12/2002 | Cosman | ........................ | 600/426 |
| 2003/0018251 A1 * | 1/2003 | Solomon | ........................ | 600/427 |
| 2003/0088189 A1 * | 5/2003 | Tu et al. | ......................... | 600/549 |
| 2003/0216639 A1 * | 11/2003 | Gilboa et al. | ................. | 600/424 |
| 2004/0019274 A1 * | 1/2004 | Galloway et al. | ............. | 600/425 |
| 2004/0024391 A1 * | 2/2004 | Cytron et al. | .................... | 606/21 |

OTHER PUBLICATIONS

Barnett, G.H., et al., Intraoperative localization using an armless, frameless stereotactic wand, J. Neurosurg., vol. 78, pp. 510-514 (Mar. 1993).
Braunstein, R.E., et al., Endoscopy and Biopsy of the Orbig, Ophthalmic Plast. Reconstr. Surg., vol. 11, No. 4, pp. 269-272 (1995).
Edwards, G., et al., Tissue ablation by a free-electron laser tuned to the amide II band, Nature, vol. 371, pp. 416-419 (Sep. 29, 1994).

(Continued)

*Primary Examiner* — Philip R Smith
(74) *Attorney, Agent, or Firm* — Tim Tingkang Xia, Esq.; Morris Manning & Martin, LLP

(57) ABSTRACT

A flexible endoscope for ophthalmic orbital surgery includes a flexible probe housing having a proximal end, a distal end and a lumen extending between the proximal end and the distal end. The endoscope also includes an image fiber disposed in the lumen that communicates image information from the distal end of the flexible probe, a purge fluid/gas port disposed at the proximal end of the flexible probe that accepts purge fluid/gas and a purge fluid/gas conduit disposed in the lumen and in fluid communication with the purge fluid/gas port. The fluid/gas conduit delivers purge fluid/gas to the distal end of the endoscope. The endoscope also includes an access conduit disposed in the lumen that receives one of an ablation instrument, a coagulating instrument and a medication delivery instrument.

7 Claims, 13 Drawing Sheets

OTHER PUBLICATIONS

Galloway, Jr., R.L., et al., Interactive Image-Guided Neurosurgery, IEEE Transactions on Biomedical Engineering, vol. 39, No. 12, pp. 1226-1231 (Dec. 1992).
Galloway, Jr., R.L., Stereotactic Frame Systems and Intraoperative Localization Devices, pp. 9-15 (1993).
Gonnering, R.S., et al., Endoscopic Laser-Assisted Lacrimal Surgery, Amer. J. of Ophthalmology, vol. 111, pp. 152-157, (Feb. 1991).
Hattenhauer, M.G., et al., The Probability of Blindness from Open-angle Glaucoma, Ophthalmology, vol. 105, No. 11, pp. 2099-2104 (Nov. 1998).
Heiduschka, P., et al., Aurintricarboxylic acid promotes survival and regeneration of axotomised retinal ganglion cells in vivo, Neuro Pharmacology, vol. 39, pp. 889-902 (2000).
Herline, A.J., et al., Image-Guided Surgery, Arch. Surg., vol. 134, pp. 644-650 (Jun. 1999).
Joos, K.M., et al., Chronic and Acute Analysis of Optic Nerve Sheath Fenestration With the Free Electron Laser in Monkeys, Lasers in Surgery and Medicine, 32:33-41 (2003).
Joos, K.M., et al., Optic Nerve Sheath Fenestration With a Novel Wavelength Produced by the Free Electron Laser (FEL), Lasers in Surgery and Medicine vol. 27, pp. 191-205 (2000).
Jordan, D.R., et al., The Synthetic Hydroxyapatite Implant: A Report on 65 Patients, Ophthalmic Plast. Reconstr. Surg., vol. 14, No. 4, pp. 250-255 (1998).
Kato, A., et al., A frameless, armless navigational system for computer-assisted neurosurgery, J. Neurosurg. vol. 74, pp. 845-849 (May 1991).
Leske, M.C., The Epidemiology of Open-Angle Glaucoma: A Review, Amer. J. of Epidemiology, vol. 118, No. 2, pp. 166-191 (1983).
Levin, L.A., Direct and Indirect Approaches to Neuroprotective Therapy of Glaucomatous Optic Neuropathy, Surv. Ophthalmol. 43 (Suppl. 1) pp. S98-S101 (Jun. 1999).
Mansour-Robaey, S., et al., Effects of ocular injury and administration of brain-derived neurotrophic factor on survival and regrowth of axotomized retinal ganglion cells, Proc. Natl., Acad. Sci. USA, vol. 91, pp. 1632-1636 (Mar. 1994).
Marcus, D.M., et al., Nucleolar Organizer Regions in Iris Nevi and Melanomas, Amer. J. of Ophthalmology, vol. 114, pp. 202-207, (Aug. 1992).
Massaro, B.M., et al., A New Approach to Nasolacrimal Duct Obstruction, Arch Ophthalmol, vol. 108, pp. 1172-1176 (Aug. 1990).
Maurer, Jr., C.R., et al., Registration of Head Volume Images Using Implantable Fiducial Markers, IEEE Transactions on Medical Imaging, vol. 16, No. 4, pp. 447-462, (Aug. 1997).
Mawn, L.A., et al., Development of an Orbital Endoscope for Use with the Free Electron Laser, Manuscript Thesis, Dept. of Ophthalmology and Visual Sciences, Vanderbilt University (2003).
Mawn, L.A., et al., Optic Nerve Sheath Fenestration in Human Cadavers Using the Free Electron Laser Through an Orbital Endoscope, Abstract (May 4, 2003).
Mawn, L.A., et al., Scanning electron microscopic examination of porous orbital implants, Abstract, Can J. Opthalmol., vol. 33, No. 4, pp. 203-209 (1998).
Morgan, J., et al., Nitric Oxide Mediates Excitotoxic and Anoxic Damage in Rat Retinal Ganglion Cells Cocultured With Astroglia, Arch Ophthalmol., vol. 117, pp. 1524-1529 (Nov. 1999).
Neufeld, A.H., et al., Inhibition of nitric-oxide synthase 2 by aminoguanidine provides neuroprotection of retinal ganglion cells in a rat model of chronic glaucoma, Proc. Natl. Acad. Sci. USA, vol. 96, pp. 9944-9948 (Aug. 1999).
Norris, J.L., et al., Bimanual Endoscopic Orbital Biopsy, Ophthalmology, vol. 92, pp. 34-38, (Jan. 1985).
Norris, J.L., et aL, Endoscopic Orbital Surgery, Amer. J. of Ophthalmology, vol. 91, pp. 249-252, (1981).
Pe'er, J., et al., Mean of the Ten Largest Nucleoli, Microcirculation Architecture, and Prognosis of Ciliochoroidal Melanomas, Ophthalmology, vol. 101, No. 7, pp. 1227-1235 (Jul. 1994).
Rahmani, B., et al., The Cause-specific Prevalence of Visual Impairment in an Urban Population, Ophthalmology, vol. 103, No. 11, pp. 1721-1726 (Nov. 1996).
Roberts, D.W., et al., A frameless stereotaxic integration of computerized tomographic imaging and the operating microscope, J. Neurosurg vol. 65, pp. 545-549 (Oct. 1986).
Stefansic, J.D., et al., Design and implementation of a PC-based image-guided surgical system, Elsevier, Computer Methods and Programs in Biomedicine, 69, pp. 211-224 (2002).
Stefansic, J.D., et al., Registration of Physical Space to Laparoscopic Image Space for Use in Minimally Invasive Hepatic Surgery, IEEE Transactions on Medical Imaging, vol. 19, No. 10, pp. 1012-1023 (Oct. 2000).
Uram, M., Ophthalmic Laser Microendoscope Ciliary Process Ablation in the Management of Neovascular Glaucoma, Ophthalmology, vol. 99, No. 12, pp. 1823-1828 (Dec. 1992).
Uram, M., Ophthalmic Laser Microendoscope Endophotocoagulation, Ophthalmology, vol. 99, No. 12, pp. 1829-1832 (Dec. 1992).
Vicinanzo, M.G., et al., Evaluation of Visualization Media for Orbital Endoscopy, Abstract, (May 4, 2003).
Wagner, A., et al., Virtual image guided navigation in tumor surgery—technical innovation, Journal of Cranio Maxillo-Facial Surgery, 23, pp. 271-273 (1995).
Weinreb, R.N., et al., Is Neuroprotection a Viable Therapy for Glaucoma?, Arch Ophthalmol. vol. 117, pp. 1540-1544 (Nov. 1999).
Yoles, E., et al., $\alpha$2-Adrenoreceptor Agonists Are Neuroprotective in a Rat Model of Optic Nerve Degeneration, Investigative Opthalmology & Visual Science, vol. 40, No. 1, pp. 65-73 (Jan. 1999).
Jordan, D.R., et al., "The Bioceramic Orbital Implant: A New Generation of Porous Implants," Ophthalmic Plastic and Reconstructive Surgery, vol. 16, No. 5, pp. 347-355.
Mawn, L.A., et al., "Development of an Orbital Endoscope for Use with the Free Electron Laser," Ophthalmic Plastic and Reconstructive Surgery, vol. 20, No. 2, pp. 150-157.

* cited by examiner

OPHTHALMIC ORBITAL SURGERY APPARATUS AND METHOD AND IMAGE-GUIDE NAVIGATION SYSTEM

CROSS-REFERENCE TO RELATED APPLICATIONS

This application claims the benefit of U.S. Provisional Patent Application No. 60/488,758, filed Jul. 21, 2003, entitled "Ophthalmic Orbital Surgery Apparatus and Method and Image-Guided Navigation System," the disclosure of which is incorporated herein by reference.

STATEMENT AS TO RIGHTS UNDER FEDERALLY-SPONSORED RESEARCH

This invention was made with government support under grant number EY13800 awarded by the National Institutes of Health. The government has certain rights in the invention.

BACKGROUND OF THE INVENTION

The present invention relates to an apparatus and method for performing ophthalmic orbital surgery, and more particularly, to a method and apparatus for performing minimally invasive ophthalmic orbital surgery using a flexible endoscope. Further, the present invention is related to a method and apparatus for performing minimally invasive ophthalmic orbital surgery using an image guided navigation system.

Endoscopy has had a tremendous impact on nearly all surgical subspecialties with the notable exception of ophthalmology. This technique began emerging when Kelling performed animal model experimental laparoscopic procedures in 1902. Therapeutic uses of endoscopy were primarily confined to gynecology until 1989 when laparoscopic cholecystectomy was introduced. Endoscopy was technically limited until the development of a video computer chip that allowed magnification and visualization of the images on a video monitors. Endoscopes currently have a wide variety of surgical applications including minimally invasive surgery in orthopedics, gynecology, otolaryngology general surgery, plastic surgery, urology and neuro-surgery. Many of these subspecialties have journals devoted specifically to endoscopic surgery. Ophthalmic applications of endoscopy have included microendoscopic ablation of the ciliary processes and other intraocular interventions. Oculoplastic surgeons currently use rigid endoscopes for small incision brow lifts and dacryocystorhinostomies. There are few reports in the literature regarding the use of endoscopes in the orbit.

The retrobulbar space remains one of the least approachable spaces in the human body. An orbitotomy, either through a medial approach disinserting the medial rectus or a lateral approach removing the zygoma and more recently through a superomedial lid crease, is the most common surgical approach to the optic nerve. Although the concept of using an endoscope in the orbit has been explored, endoscopy has not gained acceptance for intraorbital use.

An orbital endoscope was designed in the late 1970s by Norris and Clearsby. A rigid 1.7 mm diameter endoscope was developed with a lens, a 2.2 mm cannula with irrigation conduit, a 2×3 mm cannula with side port for instruments and a fiber optic ring surrounding the waveguide for intraocular surgery. Drs. Norris and Clearsby then used their endoscope in fifteen patients. They used saline to visualize the orbit which led to swelling of the tissues which decreased the endoscopic view. They noted problems of deep orbital bleeding, and pressure within the orbit from infusion of irrigating fluid. In addition, they noted that using air was not successful for visualization. Norris later refined his technique to biopsy orbital lesions for cytological analysis. Again he noted the problem of not being able to control bleeding. See Norris, J., Stewart, W., "Bimanual endoscopic orbital biopsy," *Ophthalmology*, 1985. In discussion following Dr. Norris' 1985 article, Dr. Robert Waller noted that this technique would be helpful in distinguishing between optic nerve tumors.

More recently, the Olympus HYE flexible endoscope has been used to explore the orbit in four live dogs. Hyaluronic acid was used to visualize the tissues. There has been at least one abstract report of a flexible endoscope used to perform optic nerve sheath fenestration in a cadaver.

The Free Electronic Laser (FEL) is an infrared research laser that has significant advantages over conventional lasers. Conventional lasers are limited by collateral damage and potential photochemical effects. The FEL operates at non-photochemical single-photon energies which are tunable to the vibrational modes of proteins, lipids, or water. The FEL is tunable between 2 and 9 µm with a 5 µsec macropulse structure consisting of a train of picosecond pulses spaced 350 psec apart. Wavelengths corresponding to specific molecular absorption peaks may be selected for investigation. There are presently about five free electron lasers (FELs) in the United States. Duke University houses a free electron laser studying applications in the UV range. Vanderbilt University houses one of the three tunable FELs in the United States. Vanderbilt University presently has the only FEL facility approved for human use. The Vanderbilt University FEL has been used in the 2.8-10 µm infrared spectrum. Other centers have reported using the FEL in corneal tissue. Tissue ablation at the "amide 11 band" has also been reported. A 6.45 µm (amide 11 band) wavelength has been previously experimented with in optic nerve sheath fenestration.

Optic nerve sheath fenestration has been performed through a medial orbitotomy with the FEL both in animal models and in humans undergoing enucleation. Some of these studies have been presented in abstract form and others are in preparation.

By utilizing the FEL with an endoscopic delivery system, patients would potentially benefit from minimally invasive surgery. Endoscopy has been shown in other specialties to reduce tissue trauma, improve visualization, and reduce both complications and operative time. Orbitotomies often require retraction on delicate neuro-ophthalmic tissues with the possible complications of optic nerve compression with consequent visual loss, cranial nerve palsies, and injury to the globe or ciliary ganglion. To achieve control of the orbit, extraocular muscles may need to be disinserted from the globe or bone may need to be removed. Removal of the surrounding bones of the orbit can sometimes requires a neurosurgical craniotomy to access the posterior orbit. The associated surgical risk is substantial and could be reduced with a minimally invasive procedure. In addition to the technical challenge of surgically approaching the orbit through a standard orbital technique, perioperatively patients are treated with steroids to reduce the incidence of optic nerve injury. Even short term immunosuppression with steroids can allow reactivation of latent viruses and other systemic effects. Less invasive, less traumatic orbital surgery could eliminate the need for perioperative steroid use.

The medial orbitotomy procedure requires disinserting the medial rectus and rotating the globe laterally. Possible optic nerve damage may result from a stretch injury from the lateral rotation or compression from the surgical retractors. Other postulated mechanisms of nerve injury include optic nerve ischemia vasospasm, or post-operative edema. A review of surgical outcomes in 31 patients who underwent Optical Nerve Sheath Fenestration (ONSF) showed that 40% had complications. Those patients who had previous ONSF were more likely to have a visually compromising vascular complication. In isolated case reports, two patients are described who developed total blindness following optic nerve sheath fenestration. One of these patients recovered to 20/30 over three months with only five degrees of vision and the other recovered to 20/800. Spoor reported that one ONSF postoperative death 8 hours following surgery; this death is further detailed' in an editorial by Keltner to have possibly have occurred from an arrhythmia. Corbett et al. noted a two-week postoperative death in an eighteen year old thought to be secondary to a pulmonary embolus. Decreasing the operative morbidity by reducing the surgical time, anesthetic and traction in the orbit would possibly avoid these complications and is therefore a desirable goal.

The theoretical value of using a laser through an endoscope has been recognized in the past. $CO_2$ noncontact and YAG tipped contact lasers have been advocated and used through traditional oculoplastic approaches to excise lymphangiomas, capillary hemangiomas and applied in patients with coagulation abnormalities. Orbital surgery involving vascular lesions is typically avoided because of the risks of intraoperative bleeding; conservative management of these lesions has thus been advocated in the literature. Occlusion amblyopia and significant physical deformity are recognized indications for undertaking the significant orbital risk. Intraoperative blood transfusion is sometimes necessary. Orbital lymphangiomas can be particularly difficult to excise because of the infiltration of the lesion into the normal orbital structures. Alternatives to excision of these lesions have included direct injection of medication such as steroids, sodium tetradecyl sulfate or OK-432.

A safer, more effective method to excise or medically treat these lesions may be possible with an orbital endoscope, and therefore, an endoscope which can be used effectively in orbital surgery is desirable.

For over fifty years, diagnostic images have been used for surgical guidance, especially in the field of neurosurgery. Image-guided surgery implements two fundamental ideas: first, the concept of an image-space to physical-space mapping or registration, and second, the use of an extracranial device for accurate surgical guidance without direct visualization. Such ideas gave birth to stereotactic neurosurgery, a technique for locating targets of surgical interest within the brain relative to an external frame of reference. This is traditionally defined as the temporary attachment of a mechanical frame to the skull or scalp in order to define a three dimensional (3-D) frame space around a patient. With the advent of computed tomography (CT), the coordinates of a target (i.e. tumor) in image space could be assigned coordinates in frame space if the CT images are obtained with the attached frame. Unfortunately, frames are uncomfortable to patients, must be applied prior to imaging, and are cumbersome in the imaging environment and the operating room.

These factors led to the development of frameless stereotactic surgical systems, or interactive, image-guided surgery (IIGS) systems. In traditional IIGS systems, present surgical position is tracked during an operation and displayed on pre-operatively obtained tomographic images. As the surgeon changes the current surgical position, displayed images are updated in real time. In one of the earliest IIGS systems, physical space surgical position was determined using articulated arms. The position of an articulated pointer was calculated using a personal computer (PC) and overlayed on tomographic images. Magnetic resonance images (MRI) and CT negative films are scanned into the computer and displayed as images on a video interface. Other early image-guided surgical systems also used electromechanical 3-D coordinate digitizers to indicate present surgical position on various representations of patient data, including 2-D transverse, coronal and sagittal CT or MRI slices, and on image renderings of the physical object surface. Since it was necessary to have computers capable of managing large volumes of image information (>100 Mbytes) and updating the display quickly, most early IIGS systems are were developed with VME bus devices running UNIX.

Early IIGS systems were developed on PCs using multiple processors. In a task-oriented asymmetric multiprocessing (TOAM) system developed in 32 bit extended DOS, discrete tasks such as physical space localization, data fetching, and display were conducted asynchronously on specialized processors which communicated with inexpensive, general purpose processors that worked as loaders and schedulers. For physical space localization, several articulated arms with six degrees of freedom were first developed. These cumbersome arm devices were eventually replaced with lightweight cylindrical pen-like probes which could be tracked more easily in the operating room using an optical triangulation system. The spatial location of the guidance instrument was determined using a collection of discrete processors which continually update the physical space location. This location was then passed to the central processor where it was mapped into image space. Once the image space map was complete, the appropriate tomographic slices were selected and displayed. Because this system was designed before the advent of large memory availability, image display relied heavily on hardware manipulation using disk controllers to load images directly from the hard drive. Control of the bus was passed from the main processor to the disk drive controller, where the correct image was fetched and sent to the display processor.

With the continuing increase in performance to price, processes which could only be performed on workstation class machines can now be performed on PCs. An operating room image-oriented navigation system (ORION) was developed in Windows NT using MS Visual C++ 6.0 with the Win32 API. The ORION system was designed to be faster than previous systems, but it was not necessary to redesign the software with each hardware advance. Components of the system were developed as dynamic link libraries (DLLs), so that new technology could be incorporated into the system without a complete software rewrite. The system is also somewhat portable. It runs adequately on any PC with a 200 MHz or higher Pentium processor and 128 MB of memory which also has the appropriate video card and 3-D localizer hardware and software.

When designing an image-guided surgical system, it is desirable that the precise location of an instrument used to perform image-guided surgery be determined on a continuous basis (e.g., update rates approaching 30 frames per second). Further, in an effort to ensure precision, it is desirable to continuously and accurately track the tissue being operated on during surgery. It is desirable to provide such an image-guided surgical system to track endoscopes and associated instruments during ophthalmic orbital surgical and/or investigative procedures.

BRIEF SUMMARY OF THE INVENTION

The present invention comprises a flexible endoscope for ophthalmic orbital surgery that includes a flexible probe housing having a proximal end, a distal end and a lumen extending between the proximal end and the distal end. The endoscope also includes an image fiber disposed in the lumen that communicates image information from the distal end of the flexible probe, a purge fluid/gas port disposed at the proximal end of the flexible probe that accepts purge fluid/gas and a purge fluid/gas conduit disposed in the lumen and in fluid communication with the purge fluid/gas port. The fluid/gas conduit delivers purge fluid/gas to the distal end of the endoscope. The endoscope also includes an access conduit disposed in the lumen that receives one of an ablation instrument, a coagulating instrument and a medication delivery instrument.

In another aspect, the present invention is an apparatus for collecting and processing physical space data for use while performing image-guided surgery with an instrument. The apparatus includes an endoscope, a magnetic tracking system and an image data processor. The endoscope includes a probe housing having a proximal end, a distal end and a lumen extending between the proximal end and the distal end; an image fiber disposed in the lumen that communicates image information from the distal end; a purge fluid/gas port disposed at the proximal end of the probe that accepts purge fluid/gas; a purge fluid/gas conduit disposed in the lumen and in fluid communication with the purge fluid/gas port, the conduit delivering purge fluid/gas to the distal end of the endoscope; and an access conduit disposed in the lumen which receives the instrument. The magnetic tracking system includes a magnetic tracking tip disposed proximate the distal end of the probe housing and a magnetic scanner configured to detect the magnetic tracking tip in three dimensional (3-D) space. The magnetic tracking tip generates and communicates magnetic tracking tip location data to the image data processor. The image data processor receives the magnetic tracking tip location data and determines point-based registrations to indicate surgical position in both image space and physical space based on the magnetic tracking tip location data for display while performing the image-guided surgery.

In yet another aspect, the present invention is an apparatus that includes an endoscope and a magnetic tracking system. The endoscope includes a probe housing having a proximal end, a distal end and a lumen extending between the proximal end and the distal end; an image fiber disposed in the lumen that permits image information from the distal end; a purge fluid/gas port disposed at the proximal end of the probe that accepts purge fluid/gas; a purge fluid/gas conduit disposed in the lumen and in fluid communication with the purge fluid/gas port, the conduit delivering purge fluid/gas to the distal end of the endoscope; and an access conduit disposed in the lumen which receives one of an ablation instrument, a coagulating instrument and a medication delivery instrument. The magnetic tracking system includes a magnetic tracking tip disposed proximate the distal end of the probe of the endoscope and a magnetic scanner configured to detect the magnetic tracking tip in three dimensional space.

The present invention also comprises a method of performing minimally invasive ophthalmic orbital surgery using an endoscope and an image-guided navigation system. The method includes scanning tissue of the patient using a scanning device to acquire, store and process a 3-D reference of tissue prior to the tissue being surgically exposed, wherein the image data processor creates a triangularized mesh based on the scanned tissue, determines the volumetric center of a particular portion of the tissue to be ablated, coagulated or medicated during the surgery, and implements an algorithm using the triangularized mesh and the physical space data collected by the instrument to determine the point-based registrations. The method also includes surgically exposing an area of tissue proximate the ophthalmic orbit of a patient and inserting a distal end of the endoscope into the exposed area. The endoscope has a magnetic tracking tip disposed proximate the distal end of the endoscope. The method also includes detecting the magnetic tracking tip using a magnetic scanner configured to detect the magnetic tracking tip in three dimensional space, communicating magnetic tracking tip location data to the image-guided navigation system and determining point-based registrations used to indicate surgical position in both image space and physical space; using the registrations to map into image space. Image data describing the physical space of the endoscope used to perform the image-guided surgery and the tissue.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1A:
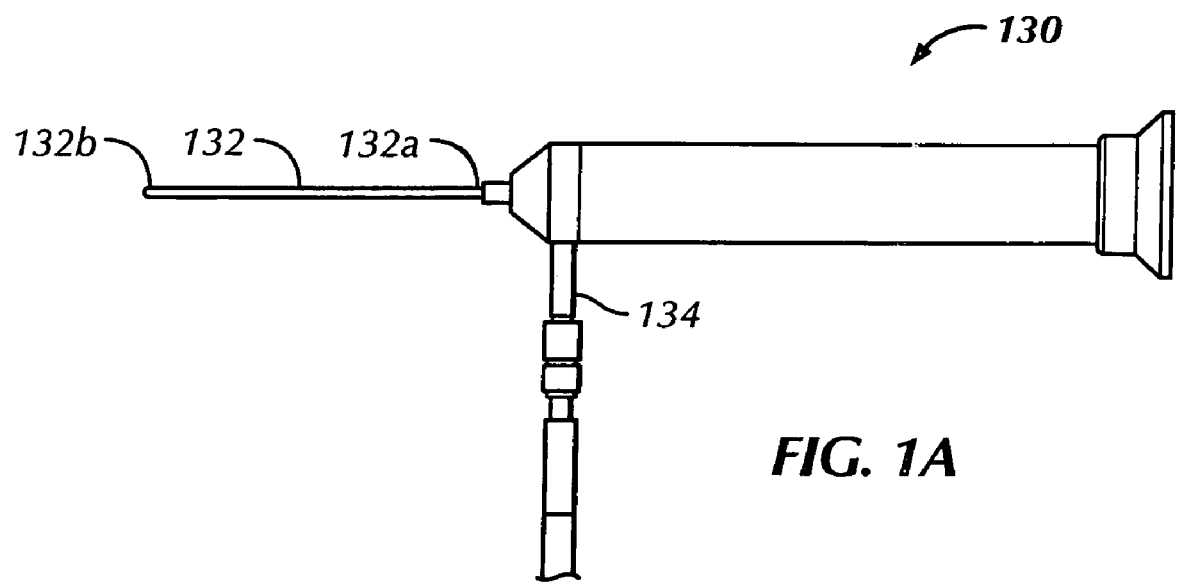
FIG. 1A is a side elevational view of a rigid endoscope for ophthalmic surgery which may be used with embodiments of the present invention.

Certain terminology is used in the following description for convenience only and is not limiting. The words "right", "left", "lower", and "upper" designate directions in the drawings to which reference is made. The words "inwardly" and "outwardly" refer direction toward and away from, respectively, the geometric center of the object discussed and designated parts thereof. The terminology includes the words above specifically mentioned, derivatives thereof and words of similar import. Additionally, the word "a", as used in the claims and in the corresponding portions of the specification, means "one" or "at least one."

Figure 13:
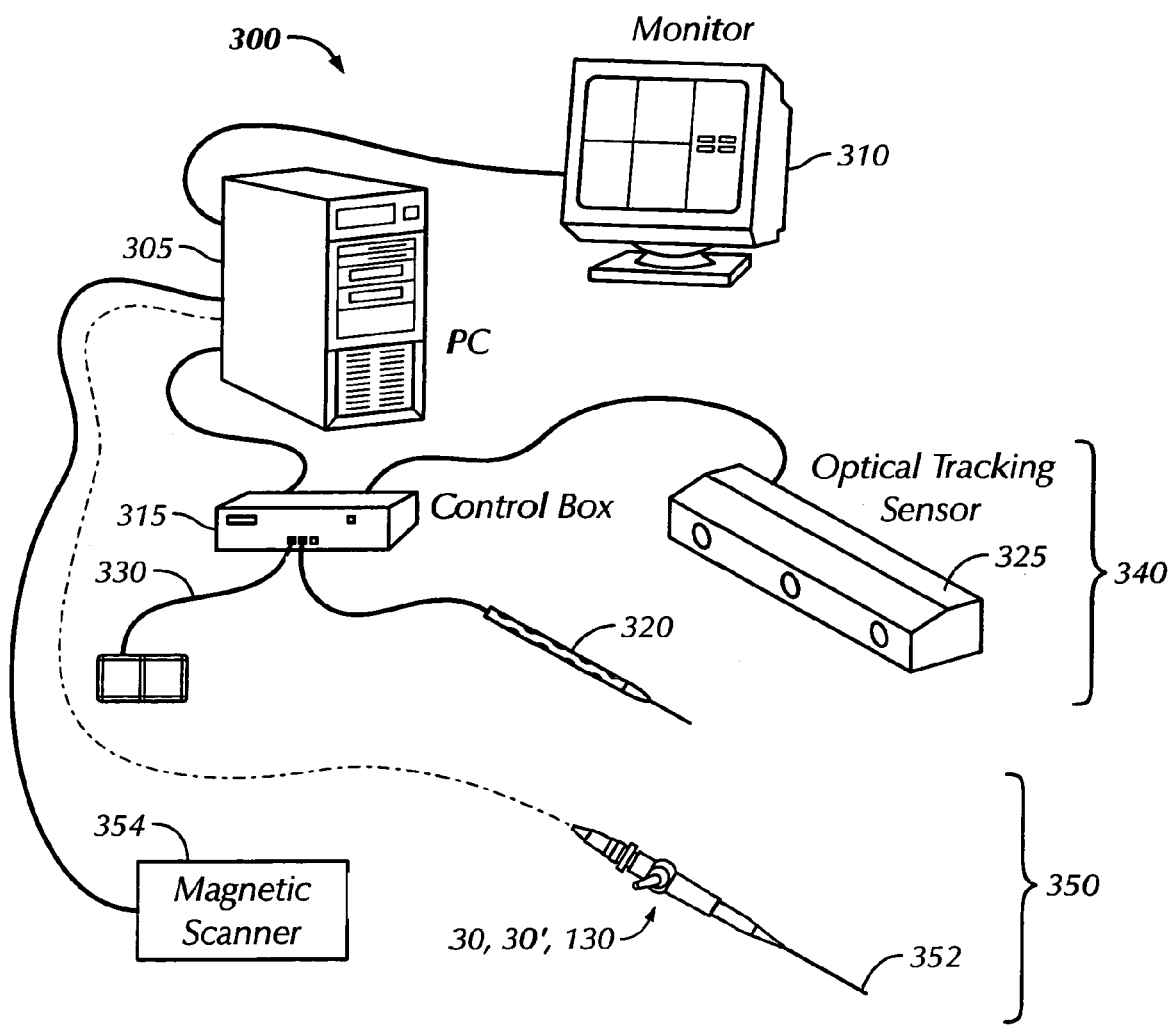
FIG. 13 shows a hardware system for one possible configuration of an image-guided tracking system in accordance with preferred embodiments of the present invention.

I. General Description:

Referring to the drawings in detail wherein like numerals represent like elements throughout, there is shown in FIGS. 2A-2B and 3-4 a rigid endoscope 130 for ophthalmic orbital surgery that includes a rigid probe housing 132 having a proximal end 132a, a distal end 132b and a lumen 132c extending between the proximal end 132a and the distal end 132b. Preferably, the rigid housing 132 has an outer diameter of less than about 3.2 mm. The rigid endoscope 130 also includes an image fiber/bundle, a purge fluid/gas port 134, a purge fluid/gas conduit and a free conduit 132d. The image fiber/bundle is disposed in the lumen 132c and permits image information from the distal end 132b to be communicated to a controller 315, a computer 305 and/or a display 310 for displaying two-dimensional (2-D) image information (FIG. 13). The purge fluid/gas port 134 disposed at the proximal end 132a of the rigid probe and accepts purge fluid/gas such as carbon dioxide ($CO_2$), saline, sodium hyaluronate and the like, for insufflation or irrigation. The purge fluid/gas port 134 may include an isolation valve or a check valve (not shown clearly) as is known in the art. The purge fluid/gas conduit is disposed in the lumen 132c and is in fluid communication with the purge fluid/gas port 134. The conduit delivers purge fluid/gas to the distal end 132b of the endoscope 132. The free conduit 132d is also disposed in the lumen 132c and can receive surgical instrument such as an ablation instrument, a coagulating instrument, forceps, scissors, a scalpel, a medication delivery device or instrument and the like. An ablation instrument may include any cutting instrument that is capable of performing fenestration.

FIGS. 2A-2B and 3-4 a flexible endoscope 30 for ophthalmic orbital surgery that includes a flexible probe housing 32 having a proximal end 32a, a distal end 32b and a lumen 32c extending between the proximal end 32a and the distal end 32b. Preferably, the flexible housing 32 has an outer diameter of less than about 3.2 mm. The flexible endoscope 30 also includes an image fiber/bundle, a purge fluid/gas port 34, a purge fluid/gas conduit and a free conduit 32d. The image fiber/bundle is disposed in the lumen 32c and permits image information from the distal end 32b to be communicated to the controller 315, the computer 305 and/or the display 310 for displaying 2-D image information (FIG. 13). The purge fluid/gas port 34 disposed at the proximal end 32a of the flexible probe and accepts purge fluid/gas such as $CO_2$, saline, sodium hyaluronate and the like, for insufflation or irrigation. The purge fluid/gas port 34 may include an isolation valve or a check valve (not shown clearly) as is known in the art. The purge fluid/gas conduit is disposed in the lumen 32c and is in fluid communication with the purge fluid/gas port 34. The conduit delivers purge fluid/gas to the distal end 32b of the endoscope 32. The free conduit 32d is also disposed in the lumen 32c and can receive surgical instrument such as an ablation instrument, a coagulating instrument, forceps, scissors, a scalpel, a medication delivery device or instrument and the like. An ablation instrument may include any cutting instrument that is capable of performing fenestration.

Figure 2A:
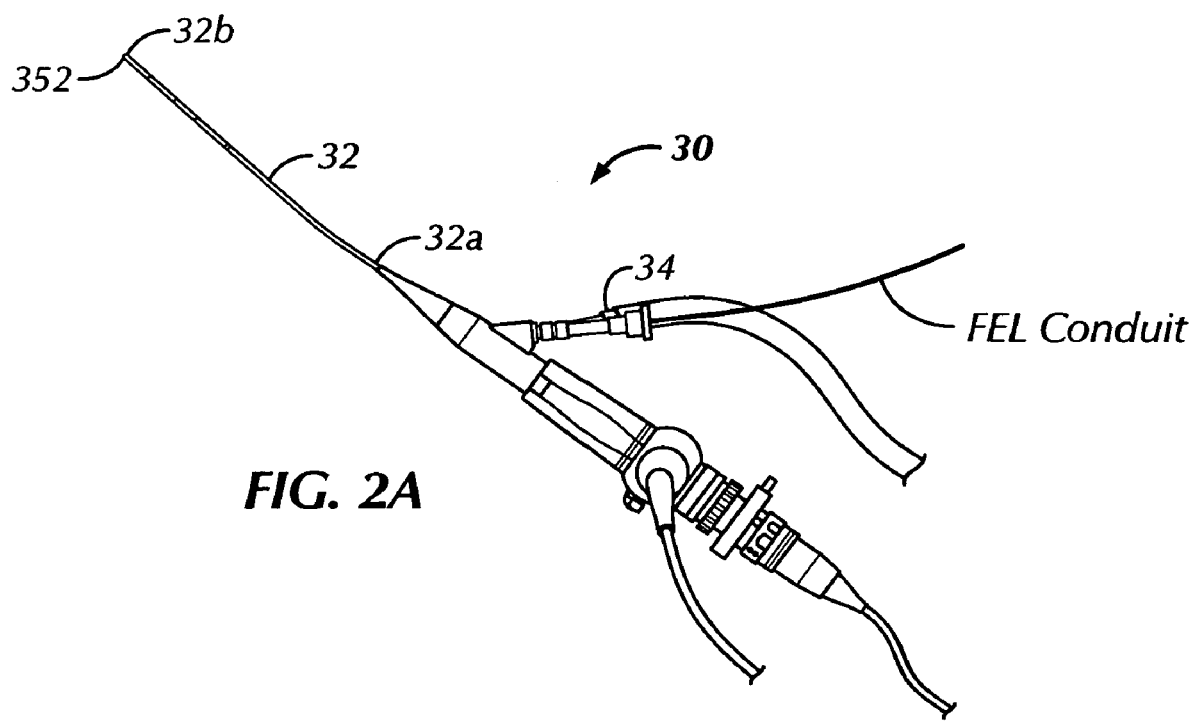
FIG. 2A is a perspective view of a flexible endoscope for ophthalmic surgery in accordance with preferred embodiments of the present invention.
Figure 2B:
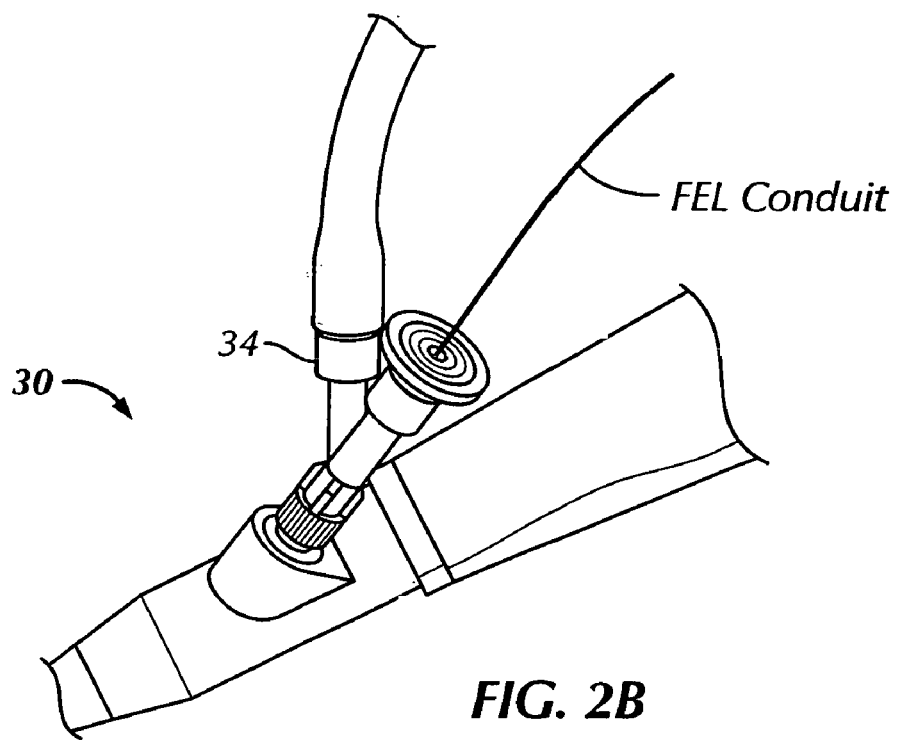
FIG. 2B is a greatly enlarged perspective view of the flexible endoscope of FIG. 2A.
Figure 5:
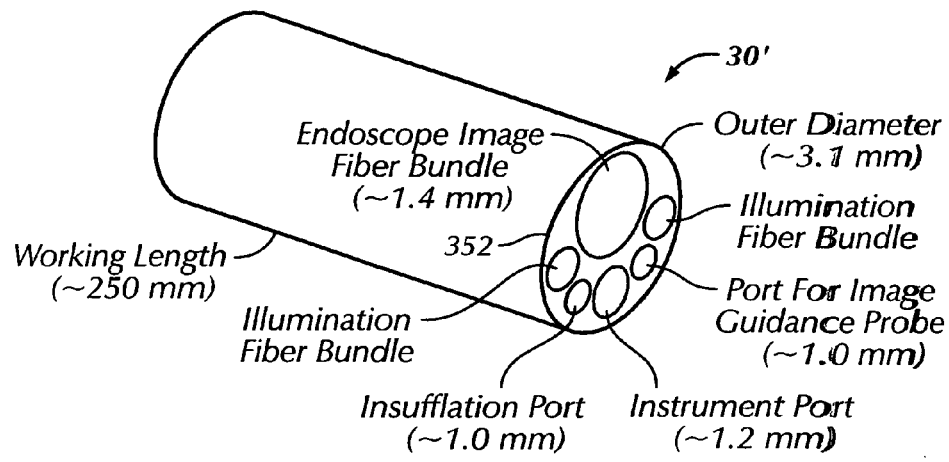
FIG. 5 is a is a greatly enlarged perspective view of an alternate embodiment of the flexible endoscope of FIG. 2A.

FIG. 5 is a is a greatly enlarged perspective view of an alternate embodiment of the flexible endoscope 30' of FIG. 2A, which includes an additional conduit for an image guidance probe, such as probe 320 (FIG. 13).

The flexible endoscope 30 and the rigid endoscope 130 are preferably used in combination with an apparatus for collecting and processing physical space data for use while performing image-guided surgery 300 (FIG. 13). The apparatus 300 includes a magnetic tracking system 350 and an image data processor 305. The magnetic tracking system 350 includes a magnetic tracking tip 352 disposed proximate the distal end 32b, 132b of the endoscope and a magnetic scanner 354 configured to detect the magnetic tracking tip in three dimensional space. The magnetic tracking tip 352 is preferably configured to generate magnetic tracking tip location data and to communicate the magnetic tracking tip location data to the apparatus for collecting and processing physical space data. The image data processor 305 receives the magnetic tracking tip location data and determines point-based registrations to indicate surgical position in both image space and physical space based on the magnetic tracking tip location data for display while performing the image-guided surgery. Preferably, location data for the magnetic tracking tip 352 includes <x, y, z> positional coordinates and orientation angles and a rotation matrix. The image data processor 305 includes a computer-readable medium holding computer-executable instructions (see e.g., FIGS. 14-15). The computer-executable instructions are used for determining the point-based registrations used to indicate surgical position in both image space and physical space based on the physical space data collected by the magnetic tracking system 350.

The present invention also includes a simplified apparatus having just the endoscope 30, 30' or 130 and the magnetic tracking system 350. The magnetic tracking system 250 includes the magnetic tracking tip 352 disposed proximate the distal end 32b, 132b of the probe 32, 132 of the endoscope 30, 30' or 130 and the magnetic scanner 354 configured to detect the magnetic tracking tip 253 in three dimensional (3-D) space.

The image-guided surgery system 300 may also include an optical tracking system 340 which determines triangulated position data based on emissions from a plurality of infrared emitting diodes (IREDs) distributed over the surface of a handle of the image guidance probe 320 or another instrument. The optical tracking system 340 includes an optical tracking sensor 325 and optionally an optical reference emitter 330. The optical tracking sensor tracks the IREDS that are disposed on the handle of the image guidance probe 320 and IREDS disposed on the reference emitter 330. The reference emitter 330 is rigidly or semi-rigidly attached to the patient by other mechanical attachment such as a bite-block or headgear for example. The IREDS are preferably distributed on the handle in a spiraling fashion. The plurality of IREDs emit a plurality of intermittent infrared signals used to triangulate the position of the image guidance probe 320 in 3-D image space. By using the point-based registrations and the triangulated position data to map into image space, image data describing the physical space of the distal end 32b of the endoscope 30 can also be used to perform the image-guided surgery and to update the image data on a periodic basis.

The optical tracking system 340 may be used as a stand-alone tracking system with the rigid endoscope 130 or flexible endoscope 30, but is preferably used in conjunction with the magnetic tracking system 350. Other image-tracking systems such as binocular-camera systems may be utilized without departing from the present invention.

The apparatus for collecting and processing physical space data 300 is preferably used with a scanning device for scanning tissue of the patient preoperatively in order to acquire, store and process a 3-D reference of tissue. The image data processor 305 creates a triangularized mesh based on the scanned tissue, determines the volumetric center of a particular portion of the tissue to be ablated, coagulated or medicated during the surgery, and implements an algorithm using the triangularized mesh and the physical space data collected by the magnetic tracking tip 352 and/or the instrument 320 to determine the point-based registrations. Preferably, the scanning device is one of a computerized tomography (CT) scanner, a magnetic resonance imaging (MRI) scanner and a positron emission tomography (PET) scanner.

Preferably, points from 3-D physical space are mapped to 2-dimensional (2-D) image space in order to be simultaneously displayed on the display with the image information collected by the flexible endoscope 30. The points from 3-D physical space may also be mapped to a 2-D endoscopic video space using a direct linear transformation (DLT). Points from 3-D physical space may alternatively be mapped to 3-D tomographic image space or endoscopic image space.

Preferably, the ablative instrument is laser delivery system. The laser delivery system includes a waveguide disposed in the lumen 32c, a laser source coupled to a proximal end 32a of the waveguide, and a lens mounted to a distal end 32b of the waveguide nearest the distal end 32b of the endoscope. The laser source may be any one of a free electron laser source, an Argon laser source, a Dye laser source, a YAG laser source and a carbon dioxide laser source. Alternatively, the ablative instrument uses one of radio-frequency waves, microwaves, ultrasonic waves, infrared waves, heat, and cryoablation in order to ablate the particular portion of the tissue. Similarly, the coagulating instrument may use one of radio-frequency waves, microwaves, ultrasonic waves, infrared waves, heat, cryoablation and a laser.

The medication delivery instrument is configured to apply dissolvable time release medication or to apply radioactive seeds. Accordingly, such medications can be placed in the inter-orbital area using minimally invasive techniques in order to treat such ailments as benign and malignant tumors or the like. The medication delivery instrument may also be a simple cannula and syringe.

In use, the flexible endoscope 30 and image-guided navigation system can be used to perform minimally invasive ophthalmic orbital surgery. Preferably, the patient is preoperatively scanned using the scanning device to acquire, store and process a 3-D reference of tissue. The image data processor 305 creates a triangularized mesh based on the scanned tissue, determines the volumetric center of a particular portion of the tissue to be ablated, coagulated or medicated during the surgery, and implements an algorithm using the triangularized mesh and the physical space data collected by the instrument to determine the point-based registrations. After scanning, an area of tissue proximate the ophthalmic orbit of a patient is surgically exposed and a distal end 32b, 132b of the endoscope 30, 130 is inserted into the exposed area. The endoscope 30, 130 has the magnetic tracking tip 352 disposed proximate the distal end 32b, 132b of the endoscope 30, 130 to permit the magnetic scanner 354 to detect the magnetic tracking tip 352 in three dimensional space within a patient. The magnetic tracking tip 352 communicates location data to the image-guided navigation system 300, and the image-guided navigation system 300 determines point-based registrations used to indicate surgical position in both image space and physical space. The registrations are used to map into image space, image data describing the physical space of the endoscope 30, 130 used to perform the image-guided surgery and the tissue. The image data is updated on a periodic basis.

II. Image-Guided Surgery:

The central tenet of image-guided surgery (IGS) and its superset, technology-guided therapy (TGT) is that a significant number of disease or disorder processes have a restricted spatial extent and that knowledge of the location and extent of that disease or disorder will allow more specific therapy. Specific therapy implies complete treatment of the disease or disorder with no therapy damage to the surrounding healthy tissue. One such system is described in U.S. Pat. No. 6,584,339 B2 (Galloway, Jr. et al.), the contents of which are incorporated by reference herein.

The process of image-guided surgery has three major components:

1. A three-dimensional (3-D) spatial localizer—a device can be freely moved in an operating room (OR), and the location and trajectory of its tip dynamically tracked. Thus, the device would return a position triplet <xp,yp,zp> for the space defined by its motion.

2. A registration technique—as with stereotaxy, the relationship between the space defined by an external device or partially external device and locations seen in the image space <xi,yi,zi> that must be determined. Instead of mapping image location into frame adjustments, <xi,yi,zi>=><xp,yp,zp>, the localizer position is mapped into image space <xp,yp,zp>=><xi,yi,zi> and that point is displayed on the appropriate image or images, such as converted scanned images. This means that all image information is retained and dynamically displayed as the surgeon moves the localizer. Thus, surgeons are able to determine not only their present surgical position but the position of all perceptible anatomic structures.

3. A means of displaying the location in image space.

Preferably, image-guided orbital surgery utilizes optical and magnetic tracking systems 345, 350 in combination. An optical tracking system 340 triangulates either selected, pulsed infrared sources, such as the Optotrak 3020 or Polaris commercially available from Northern Digital Inc., Waterloo, Ontario, Canada, or the Flashpoint commercially available from IGT/Stryker Medical, Boulder, Colo., or like reflected infrared beams such as those commercially available from Hybrid Polaris NDI.

Registration will include fiducial markers, either skin markers such as those commercially available from Medtronics, Inc., Minneapolis, Minn., or bone implant markers such as those commercially available from ZKAT, Hollywood, Fla. These markers are utilized to localize in the images using image processing routines and then touch using an optical tracker in the operating room. The positions of the fiducials are recorded and then a point registration is performed using either a quaternion based or singular-value-decomposition-based algorithm.

It is possible to mathematically position the images so as the endoscope 30, 130 with a marker is moved through the patient's anatomy, the present location can be displayed on the images.

For example, if it is desired to observe the optic nerve, the endoscope 30, 130 needs to be "navigated" behind the presently blindly navigated portions of the orbital socket behind the eyeball. The problem is, the posterior portions of the eye and orbital socket area are full of fat. However, the optic nerve can be distinguished from the fat on either computed tomography (CT) or magnetic resonance imaging (MRI). Thus, the present invention integrates the tracking in tomogram (CT or MRI) with the optical imaging from the endoscope 30, 130 in order to permit the endoscope 30, 130 to navigate the orbital socket quickly and safely.

If it is necessary to move an endoscope 30, 130 under the eyeball and move to the optic nerve in the posterior of the eye, rigid optical trackers are less desirable. Accordingly, the present invention also comprises techniques using magnetic tracking. Companies with commercially available magnetic tracking systems 350 include Aurora from NDI; Flock of Birds from Ascention; and Polhemus. Such magnetic tracking systems 350 have varying accuracies and sensitivities.

Figure 11:
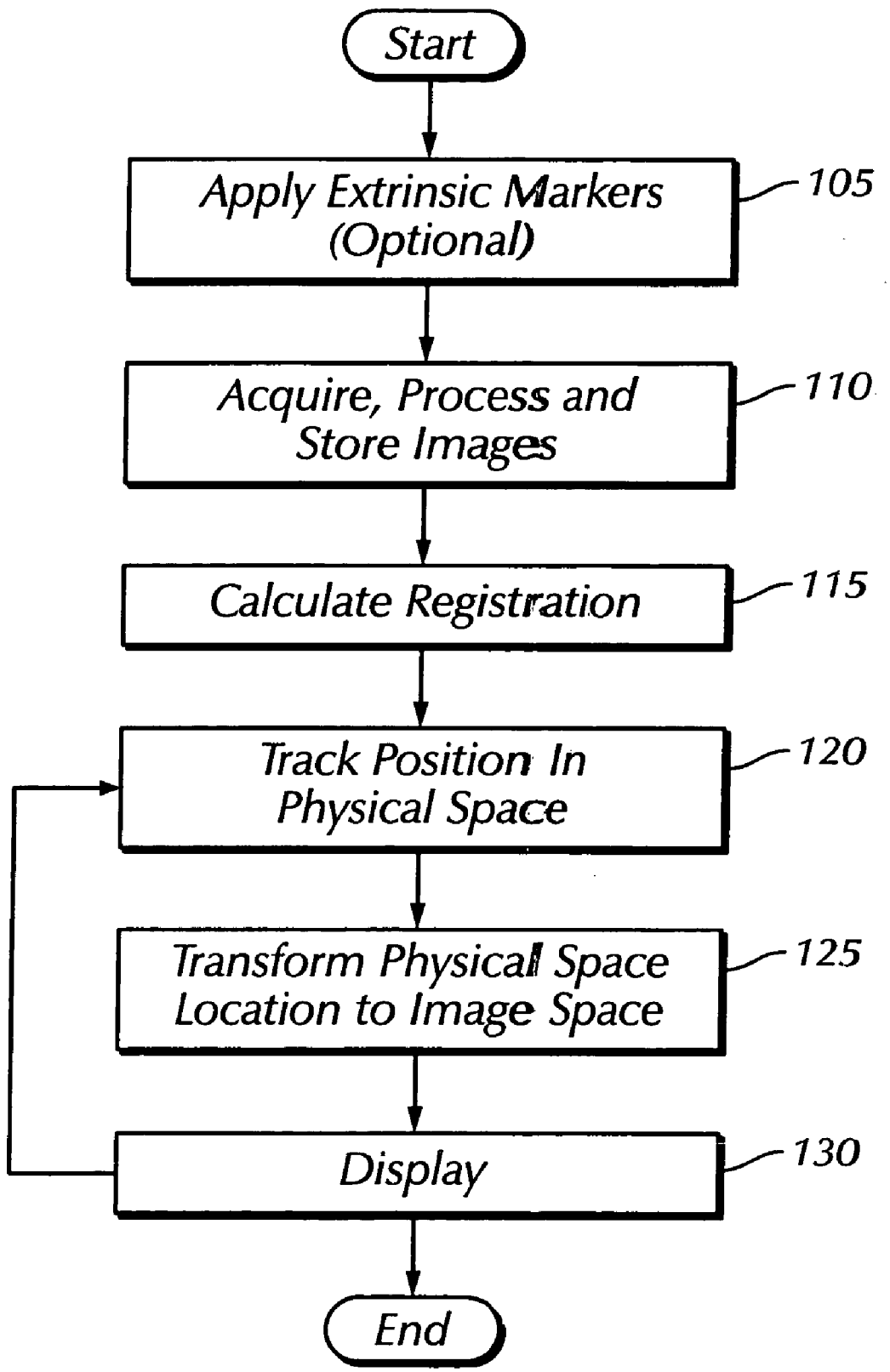
FIG. 11 shows a general flow chart for an image-guided tracking system in accordance with preferred embodiments of the present invention.

FIG. 11 shows some of the major steps involved in preparing for and performing IIGS. In step 105, it is determined if any extrinsic markers will be attached to the patient. These makers, or fiducials, are designed to be imaged and then localized in both image space and physical space for use in a point-based registration algorithm. Appropriate image volumes for a patient are then acquired, stored and processed at step 110. Most image volumes are acquired as a set of slices, 256×256 or 512×512 pixels per slice at 2 bytes per pixel with 20-200 images per volume. These images are acquired on a computerized tomography (CT) scanner, a magnetic resonance imaging (MRI) scanner or a positron emission tomography (PET) scanner. Images are typically transferred from PACS servers in radiology to image-guided surgical computers 305, where they are processed for display before surgery as necessary. Transverse, sagittal, or coronal tomographic slices require minor processing before display. In order to visualize surface renderings, a triangulated surface can be created from the volume and displayed. These triangulated surfaces can also be used in registration algorithms to map a physical surface to an image surface.

Once the surgeon has prepared and positioned the patient for surgery, patient or physical space is registered or mapped to image space at step 115 before images can be used interactively. Physical space data is collected using an instrument whose position is tracked in the operating room. For point-based registrations, corresponding points that can be localized accurately in both image space and physical space are used to create the mapping. These can include extrinsic fiducials that were attached to the patient before imaging or intrinsic fiducials which include anatomic landmarks visible in both physical and image space. For surface-based registrations, a surface of physical space points is collected and mapped onto a triangulated surface. After the accuracy of the registration is assessed, the tracked instrument 320 and/or endoscope 30, 130 is moved in physical space and the corresponding position in image space is displayed (steps 120, 125 and 130) and used as a guide during the surgical procedure.

Figure 12:
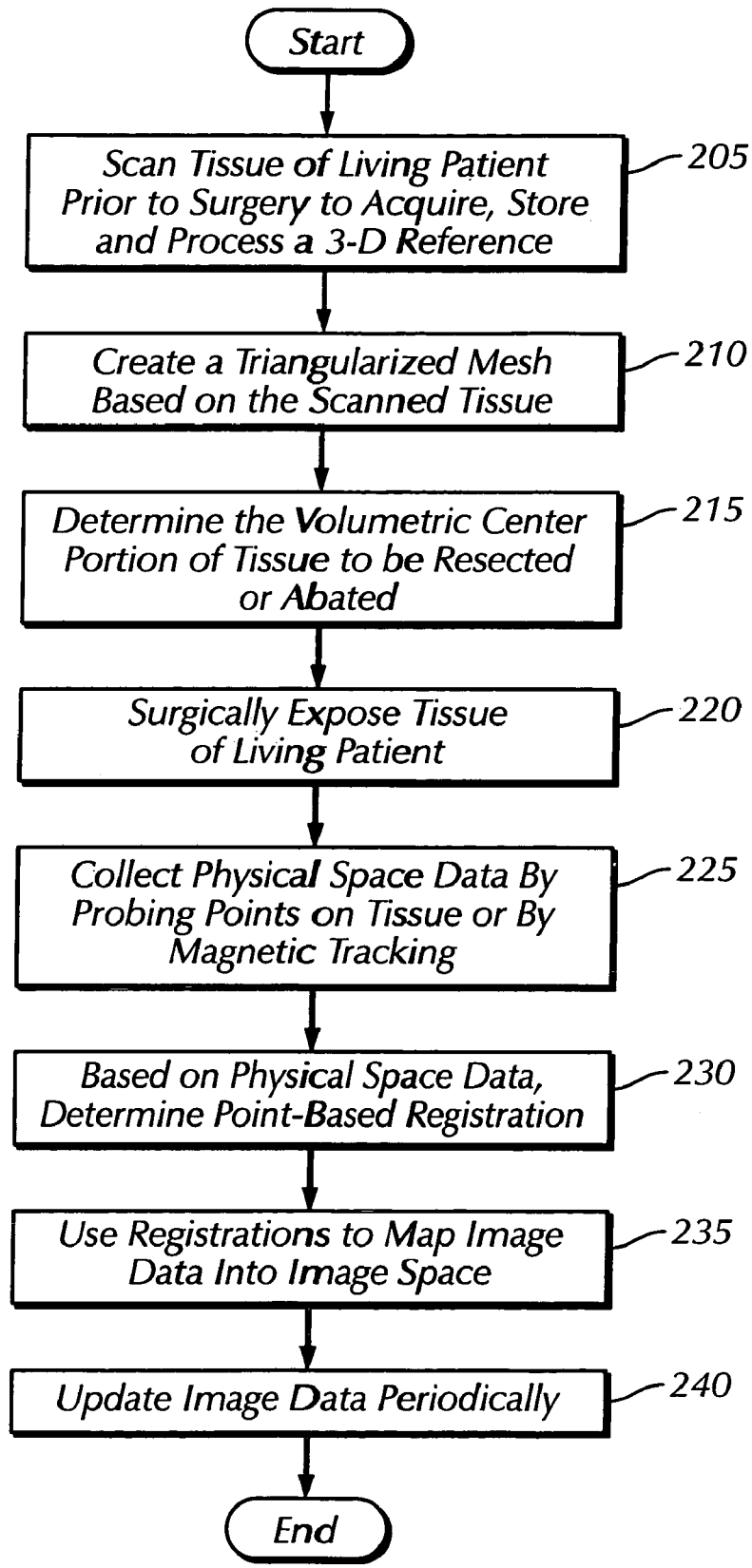
FIG. 12 shows a detailed flow chart for an image-guided tracking system in accordance with preferred embodiments of the present invention.

The present invention collects and processes physical space data for use while performing image-guided surgery, as illustrated in the flow chart of FIG. 12. Prior to surgery, tissue of the patient is scanned to acquire, store and process a 3-D reference (step 205). A triangularized mesh is then created based on the scanned tissue (step 210). The volumetric center of a particular portion of the tissue to be resected or ablated during the surgery is determined, wherein an algorithm using the triangularized mesh and the collected physical space data may be implemented to determine the point-based registrations (step 215). The algorithm may be a Besl and Mackay iterative closest point (ICP) registration algorithm. In one embodiment, physical space data is provided by probing points and in another embodiment, physical space data is provided by the magnetic tracking system described above. In another embodiment a combination of probing and magnetic tracking is utilized.

FIG. 13 shows one possible hardware system configuration 300 in accordance with embodiments of the present invention. An operating room image-oriented navigation system (ORION) may be implemented in Windows NT using MS Visual C++ 6.0 with the Win32 API. ORION was originally developed in Windows NT and is running on a 400 MHz processor Micron PC (an image data processor) 305 with 256 MB of memory and a display monitor 310. However, other operating systems and processors may be utilized. The computer 305 may also include two specialized cards such as a VigraVision-PCI card (commercially available from Visi-Com Inc., Burlington, Vt.) which is a combination color frame grabber and accelerated SVGA display controller which is capable of displaying NTSC video images in real time, and an ISA high-speed serial port card communicates with the instrument 320 via the control box 315. Of course, the computer 305 may include the necessary interfaces and graphics drivers without the need from specialized cards. For example, tracking systems 340, 350 may include network connections such as Ethernet, infrared (1R), wireless (Wi-Fi), or may include bus adapters such as parallel, serial, universal serial bus (USB) and the like.

Figure 14:
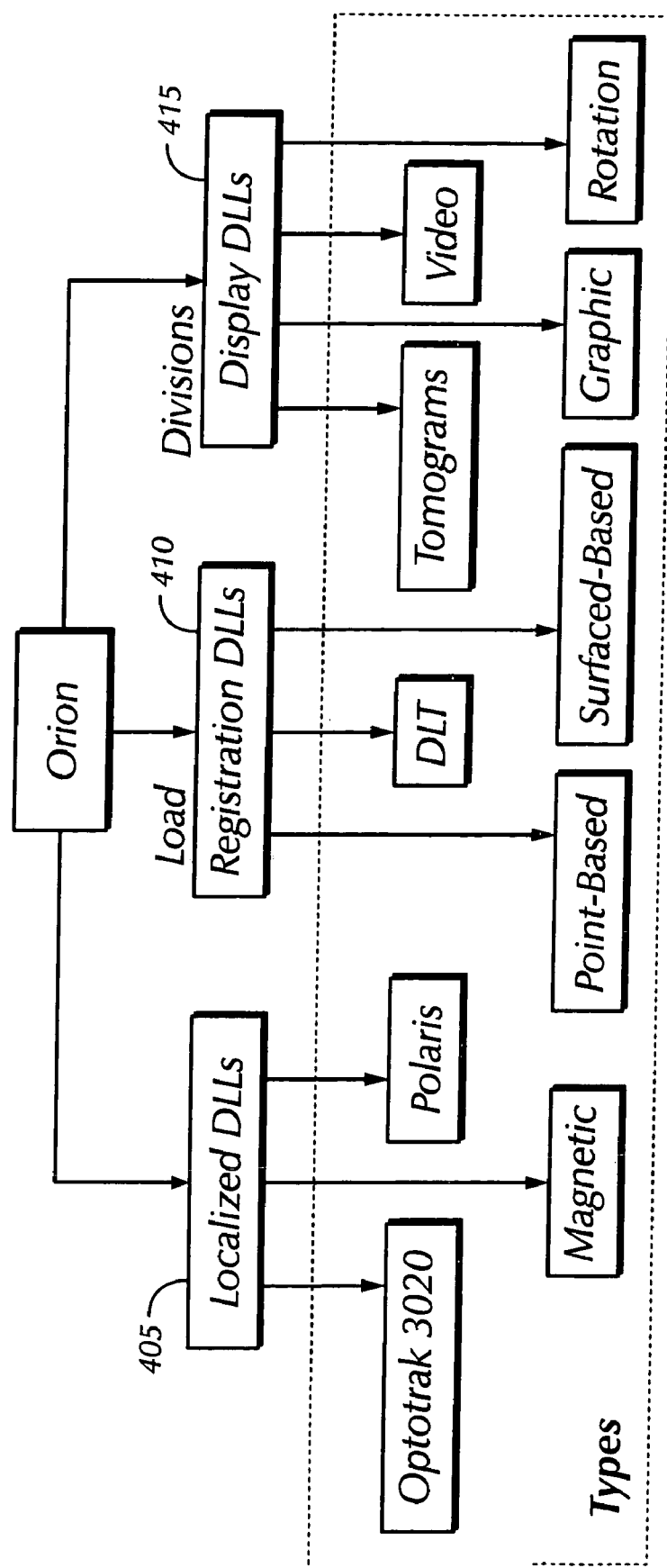
FIG. 14 shows a basic software architecture for one possible configuration of an image-guided tracking system in accordance with preferred embodiments of the present invention.
Figure 15:
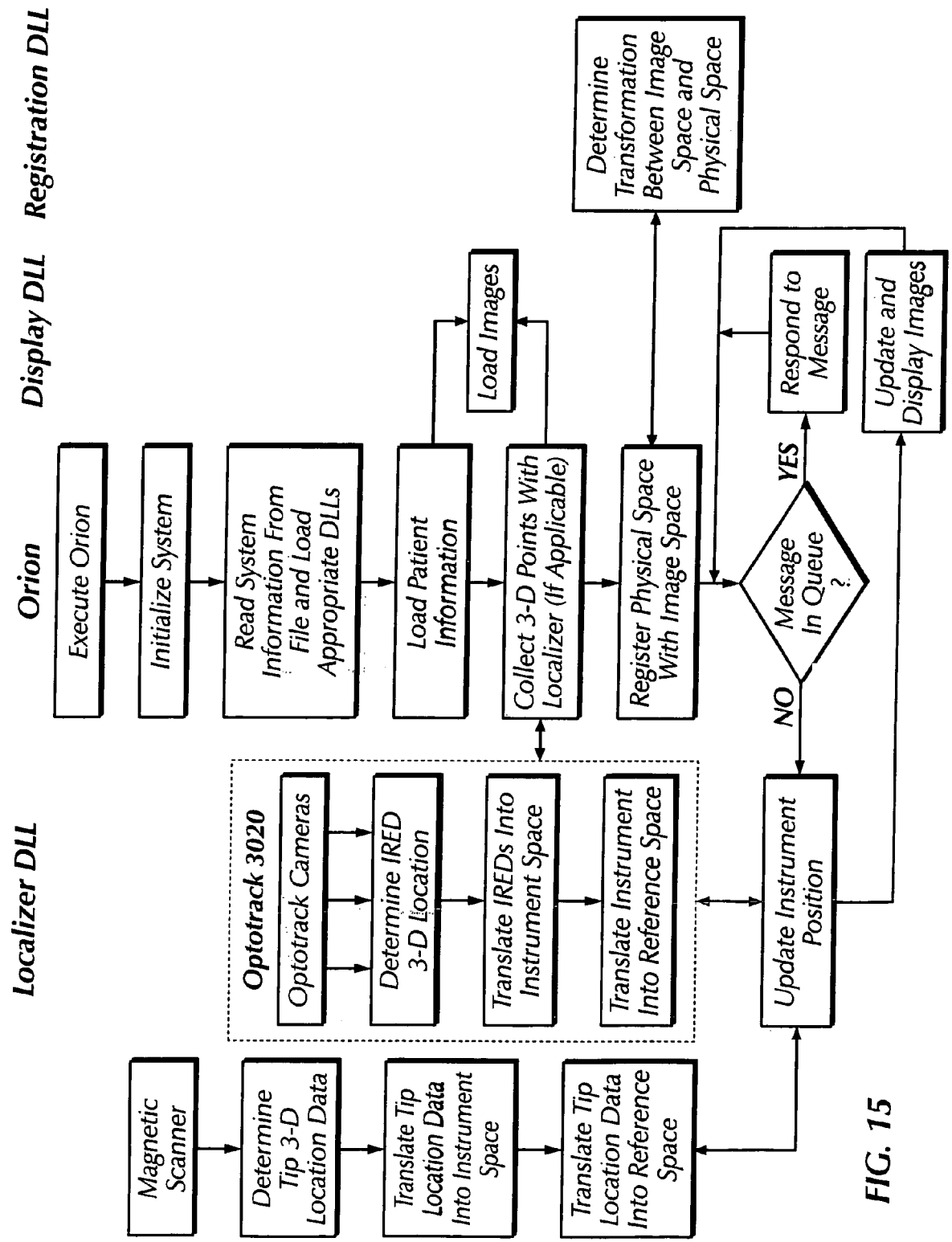
FIG. 15 shows a general flow chart for an image-guided tracking system for one possible configuration of an image-guided tracking system in accordance with preferred embodiments of the present invention.

FIG. 14 shows a basic software architecture for one possible configuration of an image-guided tracking system in accordance with preferred embodiments of the present invention. The software may include dynamic link libraries (DLLs) such as localizer DLLs 405, registration DLLs 410 and display DLLs 415. FIG. 15 shows a general flow chart for an image-guided tracking system for one possible configuration of an image-guided tracking system in accordance with preferred embodiments of the present invention.

Of course other hardware, operating systems, software packages, and image tracking systems may utilized without departing from the present invention.

III. Ophthalmic Endoscope Surgery Experiment:

Previous studies have shown that the Amide II wavelength (6.45 µm) produced by the FEL can efficiently create an optic nerve sheath fenestration in (ONSF) rabbits. The FEL has been used to perform optic nerve sheath fenestration in monkeys and in humans undergoing enucleation (unpublished data). An experiment was conducted to demonstrate the feasibility of an orbital endoscope for use with FEL in accordance with preferred embodiments of the present invention. The experiment utilized a laser delivery system through a flexible endoscope 30 in accordance with an embodiment of the present invention which was performed on two adult pig cadavers and two fresh human cadavers that had orbital endoscopy performed to develop a method of ONSF with the FEL. Visualization media and surgical techniques were compared.

An optic nerve sheath fenestration was performed using the FEL (6.45 µm, 30 Hz, 2-3 mJ, 250 µm spot size) through a glass hollow waveguide introduced through an endoscope in a human cadaver. Visualization of the orbital structures was excellent with carbon dioxide. A dural window was made using the FEL through a glass hollow waveguide adapted to a modified endoscope such as the Olympus HYE-XP endoscope commercially available from Olympus America, Inc., Lake Success, N.Y. 11042. Histologic evidence of the optic nerve sheath fenestration was produced.

A hollow waveguide capable of transmitting the FEL through an endoscope was constructed. Optic nerve sheath fenestration using the FEL applied via an endoscope is technically feasible. Additional studies are currently examining techniques to improve intraorbital endoscopic laser use.

The experimental study was performed to determine if the orbit could be visualized with a modified commercially available flexible endoscope 30, construct a FEL delivery hollow waveguide which could be introduced into the orbit through this endoscope and then use the FEL to make a fenestration in the optic nerve dural sheath. The engineering aspects of the project include developing both a laser probe and a method to apply it through an endoscope. The surgical aspects of the project include using the modified endoscope in cadaver orbits, testing visualization media and using the designed laser delivery system to perform an optic nerve sheath fenestration in a fresh cadaver. The engineering aspects of the project include the creation of both a laser waveguide and also a lens over stainless steel tubing to house the waveguide. The lens will both protect the laser waveguide from water and provide focusing of the laser beam.

Two cadaver pig heads and two human cadavers were used for this study. Both the Vanderbilt Institutional Animal Care and Use Committee and the Vanderbilt Institutional Review Board approved the study. The pigs were frozen decapitated specimens. Prior to experimentation, the frozen specimens were thawed. The human cadavers were fresh adult specimens.

Figure 1B:
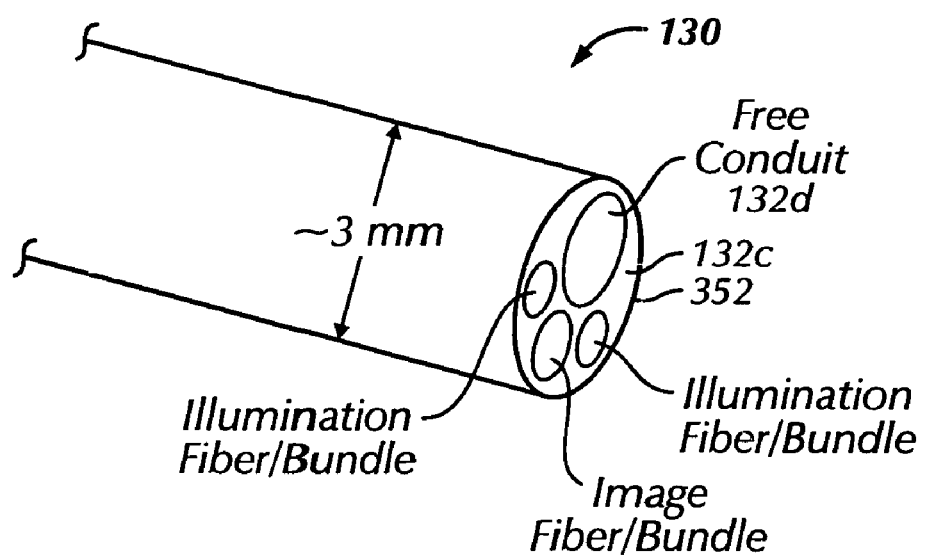
FIG. 1B is a perspective cross-sectional rendering of the rigid endoscope of FIG. 1A.
Figure 3:
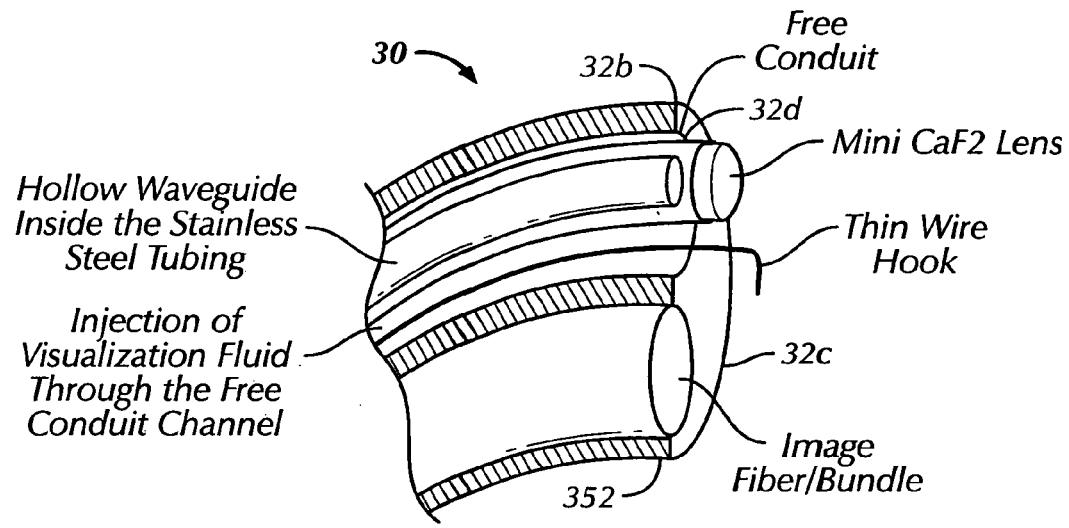
FIG. 3 is a greatly enlarged perspective cross-sectional view of the flexible endoscope of FIG. 2A.
Figure 4:
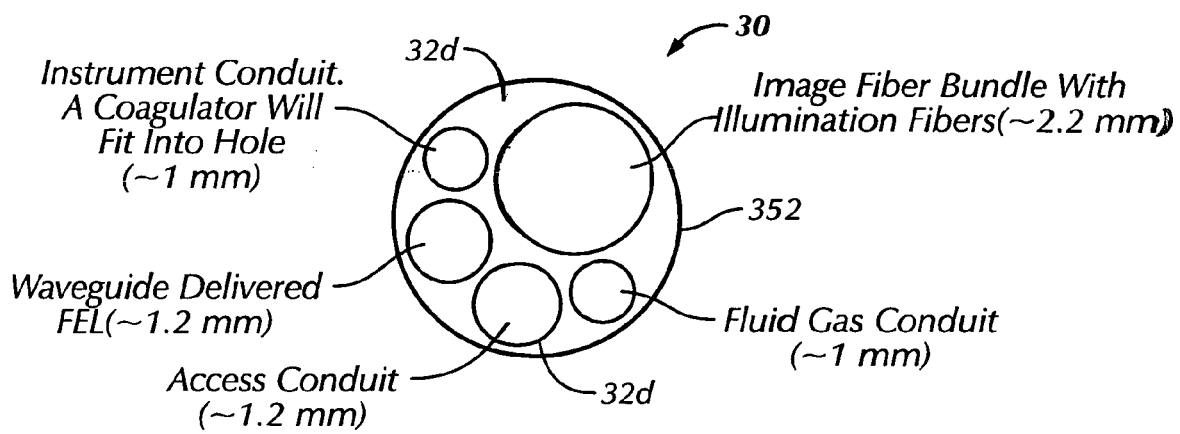
FIG. 4 is a greatly enlarged front elevational cross-sectional view of the flexible endoscope of FIG. 2A.

The modified HYE type P-Hysterofibroscope was used for all of the surgical procedures. Of course other commercially available or custom manufactured endoscopes could be utilized without departing from the present invention. The unmodified endoscope has been FDA approved and is commercially available for surgery (FIG. 2A). The endoscope has an outer diameter of 3.1 mm, and includes a 1.4 mm endoscope fiber/bundle, and a 1.2 mm diameter free conduit. The image fiber has a viewing angle of 100°, and focus depth from 1 to 30 mm. To modify this endoscope, a FEL delivery hollow waveguide was created to fit into the free conduit (FIGS. 2B-2C and 3-5). A hollow waveguide was constructed and then fit into thin stainless steel tubing. A "mini" lens was fixed in front of the stainless steel tubing. A video camera monitoring system, light source, printer and high-flow electronic $CO_2$ insufflator were used in the experiments (FIG. 3). Endoscopic, images were viewed on a CCTV video connection and all procedures were videotaped. An endoscopic valve was used to facilitate simultaneous instillation of visualization media and instruments through the free conduit, such as the Sureseal® 11 which is commercially available from Applied Medical Resources Corp., Rancho Santa Margarita, Calif. 92688 (FIG. 1). A 70 mm working length cannula/trocar system 100 was also used, such as the type commercially available from United States Surgical, Tyco Healthcare Group LP. Norwalk., Conn. 06856 (FIG. 4).

The experiments were carried out with approval from both the Institutional Animal Care and Use Committee and Institutional Review Board. In the first pig model a lateral orbitotomy was performed. After a lid speculum was placed, an inferior lateral fornix conjunctival peritomy of approximately 3 mm was made using 0.5 forceps and Wescott scissors in the porcine orbit. Blunt dissection with Steven's tenotomy scissors was performed to open the inferior lateral quadrant. The endoscope was introduced through the conjunctival incision. Sodium hyaluronate was infused via a cannula through the instrument channel of the endoscope and the orbit was visualized. In the other orbit a similar incision was made and saline was infused through the free conduit of the endoscope. Following, the surgery, open dissection of the orbit was performed and the globes were enucleated to determine the adequacy of the surgical approach.

For the second swine experiment, saline was used for both orbits. Medial and lateral incisions were compared. The 1.2 mm reusable biopsy cup forceps were used to attempt removal a section of the optic nerve dural sheath. The globes were also enucleated following the experimental trial for gross inspection and dissection of the orbit.

For the first human cadaver, the right orbit was approached through an inferior medial periotomy of approximately 3 mm. The quadrant was cleared with tenotomy scissors. The endoscope was introduced. Saline was infused as a visualization media. Olympus biopsy forceps were used to attempt removal of a piece of the optic nerve sheath. The surgery on the left orbit was performed in the FEL operating suite so that the free electron laser could he trialed for optic nerve sheath fenestration. Following the procedure, the globes were enucleated.

Figure 6:
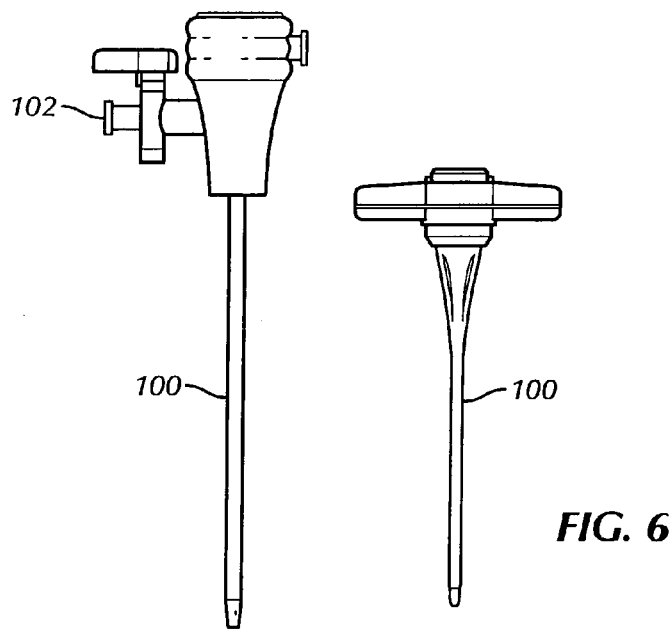
FIG. 6 is a cannula/trocar system with and without isolation and/or insufflation valves which may be used in conjunction with the present invention.
Figure 7A:
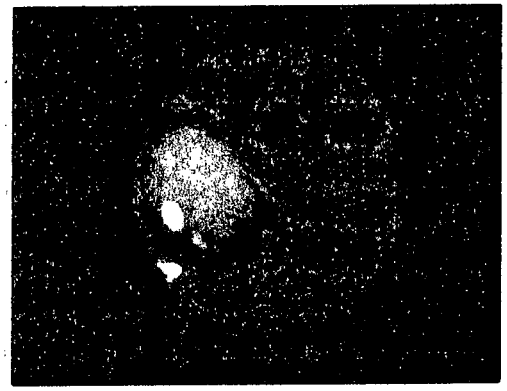
FIGS. 7A-7D are images of an orbital area visualized through the flexible endoscope of FIG. 2A.
Figure 7B:
Figure 7C:
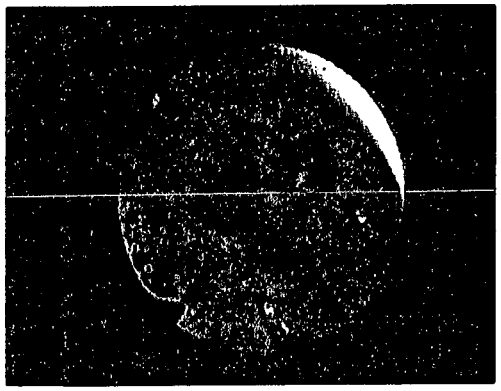
Figure 7D:
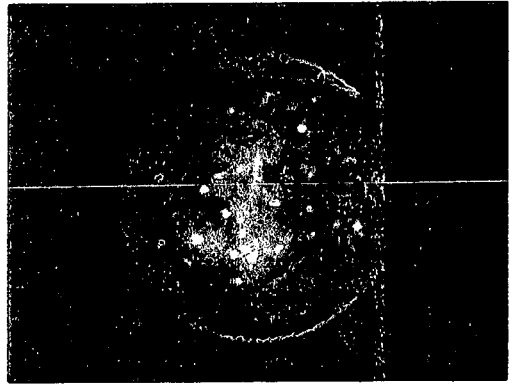
Figure 8A:
FIGS. 8A-8D are images of various fenestrations of an optic nerve performed by and visualized through the flexible endoscope of FIG. 2A.
Figure 8B:
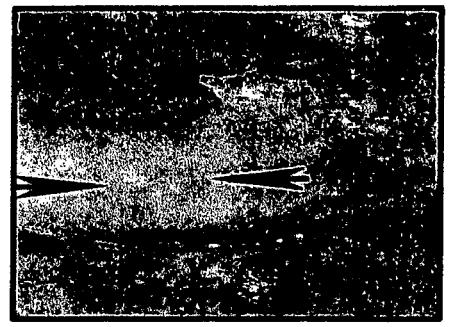
Figure 8C:
Figure 8D:
Figure 9A:
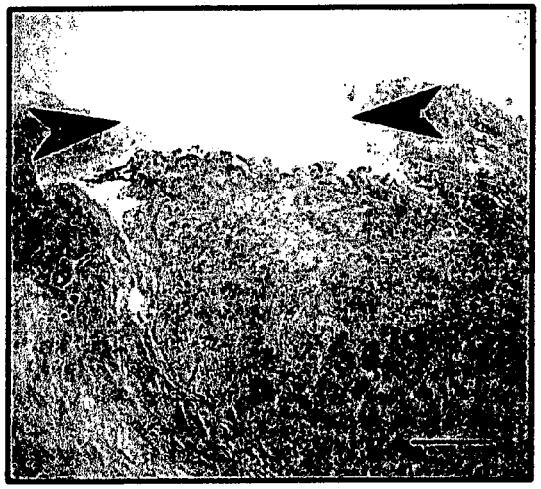
FIGS. 9A-9C are tomographic scans demonstrating various fenestrations of an optic nerve as performed by the flexible endoscope of FIG. 2A.
Figure 9B:
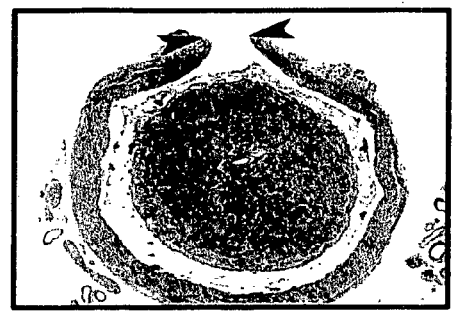
Figure 9C:
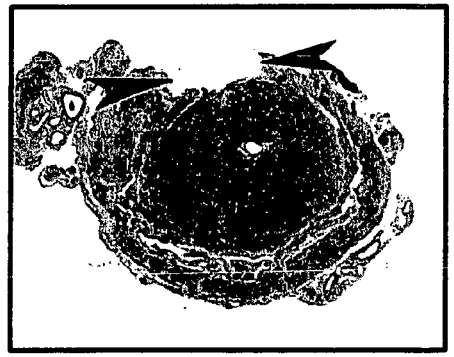
Figure 10A:
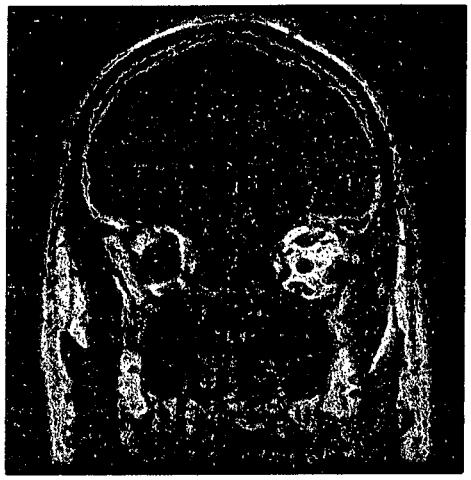
FIGS. 10A-10C are tomographic scans demonstrating before and after effects of an orbital surgical procedure.
Figure 10B:
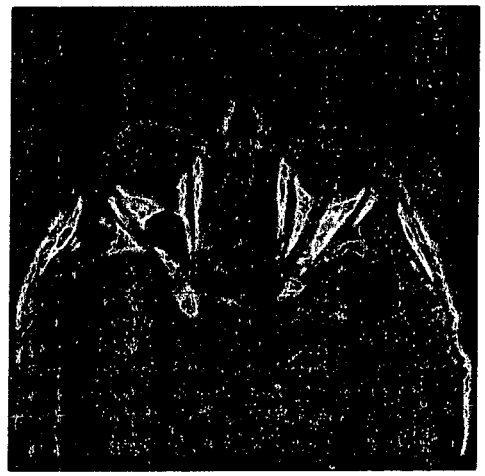
Figure 10C:
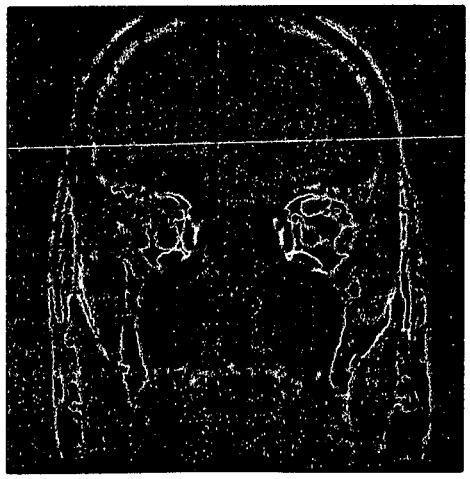

In the second human cadaver, the insufflation and access needle was introduced in the inferior medial orbit. The gas tubing was attached to the stopcock 102 (FIG. 6) and the orbit was inflated with $CO_2$ gas with a pressure of 5 mmHg. The trocar/cannula system 100 (FIG. 6) was placed following insufflation of the orbit. The endoscope 30, 130 was then inserted through the cannula. The orbit was well visualized. Because the cannula/trocar system 100 limited the mobility of the endoscope 30, 130 in the orbit, the cannula/trocar system 100 was removed from the cavity. The gas was attached to the free conduit of the endoscope 30, 130. The endoscope 30, 130 was introduced through the entry site. The orbit was visualized and structures successfully identified (FIG. 7). The endoscopic valve was then attached to the free conduit of the endoscope 30, 130. The gas was attached to the open sideport of the endoscopic valve. The waveguide was introduced through the endoscopic valve. Energy levels were determined using an energy meter just prior to and immediately after lasing, such as the one commercially available from Molectron Detector, Inc Portland, Oreg. The FEL beam was transmitted via vacuum pipes to nitrogen purge gantry and then to the hollow waveguide connector. The laser optic nerve sheath fenestration was performed (FIGS. 8A-8D and 9A-9C). Following the incision of the dural sheath with the laser the dural window was lifted from the sheath with the biopsy cup forceps. Fiduciary markers were then placed on the cadaver and orbital computed tomography (CT scan) was performed to image the left orbit.

The globe and optic nerves were grossly inspected from the pig trials. Following the human trials the globes and optic nerve specimens were removed and placed in formalin, such as the one commercially available from Pen-Fix, Richard-Allan Scientific, Kalamazoo, Mich. The specimens were then examined under the dissecting microscope. The area with the laser incised optic nerve dural window was photographed.

Efficient identification of the optic nerve was not possible in all cadaver specimens. The thawed frozen pigs were a difficult model for this procedure; the fat was firm and not easily displaced. Distinguishing between the orbital structures was extremely difficult as all the structures were a yellow white color and it was not possible to confidently determine the anatomical features. When visualization was attempted with hyaluronic acid, the healon regurgitated through the incision and did not displace the fat. The saline infusion caused ballooning of the orbital fat. However, saline did allow for better visualization of the images via the endoscope 30, 130 than did the hyaluronic acid. There was no surgical difference between performing the procedure through the lateral or medial approach in the cadaver pigs. The biopsy forceps were used to remove a dural window from the optic nerve in the pig and the dura could not be removed.

In the first human trial the saline visualization gave a reasonable view of the anatomy; however the fat billowed in front of the lens of the endoscope 30, 130 and obscured the image. The fat also became hydrated with the saline making the procedure more difficult with time. Intraoperative orientation and directional manipulation of the endoscope 30, 130 in the orbit was difficult. Biopsy cups were used in the right orbit and could not pierce the dural covering to fenestrate the nerve. When the second orbit was explored, the nerve was localized and the laser attempted. The mini lens was displaced off the front of the hollow waveguide allowing the laser wire to advance past the guide. This necessitated that the laser procedure be aborted. A second fenestration was attempted with the biopsy forceps without success.

In the second human cadaver the endoscopic valve was utilized to facilitate simultaneous instillation of visualization media and instrumentation. This improved the ease of instrument manipulation. The insufflator and access needle did not traumatize the globe or orbital structures and aided in entry into the orbit. This unit functions as a spring loaded needle with a blunt stylet. When the needle is pressed against the conjunctiva and tenon's the needle is exposed. Once through tenon's the loss of resistance causes the blunt stylet to appear. However, the pediatric abdominal 70 mm long, ⅔ mm diameter trocar for endoscopy was too long to use in the orbit and restricted the movement of the endoscope 30, 130 in the orbit. The conjunctival wound had to he held closed to prevent leakage of gas. Orientation and directional manipulation of the endoscope 30, 130 continued to increase the operative time. The $CO_2$ gave an extremely clear view of all the orbital structures, which were easily distinguished. However, knowing how much of the endoscope 30, 130 to introduce and which direction to proceed through the orbital fat with the endoscope 30, 130 was more difficult than predicted based on the anatomy. It was determined that the endoscope 30, 130 needed to be directed toward the nerve when less than 25 mm of the tip was inserted into the wound. The $CO_2$ also caused minimal disruption of the anatomical planes while using the endoscope 30, 130. The optic nerve was obvious within the muscle cone (FIG. 7). Vessels were apparent and could be avoided. In the fresh cadaver blood filled vessels bled if traumatized and minimal tissue trauma occurred. The created hollow waveguide was easy to direct toward the optic nerve through the endoscope 30, 130, caused no bleeding and made a visible incision in the dura.

Thus, visualization media and surgical techniques were experimented with to develop an endoscopic approach to the optic nerve. A successfully designed and used hollow waveguide and laser delivery system for the FEL through an endoscope 30, 130 has been demonstrated.

But, in the orbital endoscopy experiment above, intraoperative orientation and directional manipulation of the endoscope 30, 130 in the orbit was difficult. The obstacle of intraoperative orientation has also been encountered in other surgical fields such as neurosurgery. These obstacles fueled the development of navigational systems for image guided surgery. Current research in neurosurgery includes superimposing three-dimensional information on live video sequences. Other advances in endoscopic neurosurgery include a "red-out module" or virtual anatomic landscape which allows a surgeon to achieve hemostasis if total visualization is lost because of hemorrhage. Surgical instruments, including the endoscope 30, 130 can be used as positional tracking devices. A fiduciary navigational system would significantly improve the fidelity of orientation in the orbit, reduce the operative time and risk.

From the foregoing, it can be seen that the present invention comprises an apparatus and a method for performing minimally invasive ophthalmic orbital surgery using a flexible endoscope and an apparatus and a method for performing minimally invasive ophthalmic orbital surgery using an image guided navigation system with either rigid or flexible endoscopes. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An apparatus for collecting and processing physical space data for use while performing image-guided surgery with an instrument, the apparatus comprising:
   (a) an endoscope including:
      (i) a probe housing having a proximal end, a distal end and a lumen extending between the proximal end and the distal end;
      (ii) an image fiber disposed in the lumen that communicates image information from the distal end;
      (iii) a purge fluid/gas port disposed at the proximal end of the probe that accepts purge fluid/gas;
      (iv) a purge fluid/gas conduit disposed in the lumen and in fluid communication with the purge fluid/gas port, the conduit delivering purge fluid/gas to the distal end of the endoscope; and
      (v) an access conduit disposed in the lumen which receives the instrument;
   (b) a magnetic tracking system that includes a magnetic tracking tip disposed proximate the distal end of the probe housing and that is configured to detect the magnetic tracking tip in a three dimensional (3-D) physical space; and
   (c) an image data processor configured to
      obtain an image space having a plurality of tomographic images each containing all image information;
      determine point-based registrations mapping the 3-D physical space to the image space based on points in the 3-D physical space and corresponding points in the image space;
      determine a location and an orientation of the instrument in the image space based on magnetic tracking tip location data generated by the magnetic tracking tip in the 3-D physical space and the point-based registrations; and
      dynamically display, while performing the image-guided surgery, (i) a selected one of the plurality of the tomographic images that overlaps the location of the instrument in the image space and (ii) indications of the location and orientation of the instrument in the image space.

2. The apparatus of claim 1, further comprising:
   (d) a scanning device for scanning tissue of the patient to acquire, store and process a 3-D reference of tissue prior to the tissue being surgically exposed, wherein the image data processor creates a triangularized mesh based on the scanned tissue, determines the volumetric center of a particular portion of the tissue to be ablated, coagulated or medicated during the surgery, and implements an algorithm using the triangularized mesh and the physical space data collected by the instrument to determine the point-based registrations, wherein the instrument is configured to transmit a free electron laser (FEL) that surgically ablates a particular portion of a tissue.

3. The apparatus of claim 2, wherein the scanning device is one of the following scanners: a computerized tomography (CT) scanner, a magnetic resonance imaging (MRI) scanner and a positron emission tomography (PET) scanner image space, wherein the instrument includes a laser delivery system including a waveguide and a lens mounted to a distal end of the waveguide adjacent to the distal end of the endoscope, wherein a proximal end of the waveguide is coupled to a laser source, wherein the laser source that is a FEL source generating FEL in a predetermined wavelength range including 6.45 µm, wherein the waveguide is a glass hollow waveguide adapted for transmitting FEL in a predetermined wavelength range including 6.45 µm.

4. The apparatus of claim 1, wherein the magnetic tracking tip location data includes <x, y, z>positional coordinates and orientation angles and a rotation matrix, wherein the image space includes scanned images that are previously obtained, wherein the image data processor provides the scanned images for display while the image-guided surgery is being performed, wherein the instrument is configured to transmit a free electron laser that surgically ablates a particular portion of a tissue.

5. The apparatus of claim 1, wherein points from 3-D physical space are mapped to 2-dimensional (2-D) image space, wherein the instrument includes a laser delivery system including a waveguide and a lens mounted to a distal end of the waveguide adjacent to the distal end of the endoscope, wherein a proximal end of the waveguide is coupled to a laser source, wherein the laser source that is a free electron laser (FEL) source generating FEL in a predetermined wavelength range including 6.45 µm, wherein the waveguide is adapted for transmitting FEL in a predetermined wavelength range including 6.45 µm.

6. The apparatus of claim 5, further comprising a display device, wherein the display device is configured to display the 2-dimensional image space.

7. The apparatus of claim 6, wherein the display device is operatively connected to the endoscope.

* * * * *